(12) United States Patent
Walker et al.

(10) Patent No.: US 8,548,759 B2
(45) Date of Patent: Oct. 1, 2013

(54) METHODS, APPARATUS, OR SYSTEMS FOR CHARACTERIZING PHYSICAL PROPERTY IN NON-BIOMATERIAL OR BIO-MATERIAL

(75) Inventors: William F. Walker, Charlottesville, VA (US); Francesco Viola, Charlottesville, VA (US); F. William Mauldin, Charlottesville, VA (US)

(73) Assignees: University of Virginia Patent Foundation, Charlottesville, VA (US); HemoSonics, LLC, Charlottesville, VA (US)

( * ) Notice: Subject to any disclaimer, the term of this patent is extended or adjusted under 35 U.S.C. 154(b) by 511 days.

(21) Appl. No.: 12/940,838

(22) Filed: Nov. 5, 2010

(65) Prior Publication Data
US 2011/0137588 A1 Jun. 9, 2011

Related U.S. Application Data (60) Provisional application No. 61/258,949, filed on Nov. 6, 2009, provisional application No. 61/286,605, filed on Dec. 15, 2009.

(51) Int. Cl.
*G01F 17/00* (2006.01)
*G06F 11/30* (2006.01)

(52) U.S. Cl.
USPC .............. 702/56; 702/182; 702/183; 702/189

(58) Field of Classification Search
USPC .................. 702/56, 104, 116–118, 182, 183, 702/188, 189
See application file for complete search history.

(56) References Cited

U.S. PATENT DOCUMENTS

| | | | |
|---|---|---|---|
| 5,487,387 A | 1/1996 | Trahey et al. |
| 5,673,699 A | 10/1997 | Trahey et al. |
| 5,903,516 A | 5/1999 | Greenleaf et al. |
| 5,921,928 A | 7/1999 | Greenleaf et al. |
| 5,991,239 A | 11/1999 | Fatemi-Booshehri et al. |
| 6,039,691 A | 3/2000 | Walker et al. |
| 6,371,912 B1 | 4/2002 | Nightingale et al. |
| 6,692,439 B1 | 2/2004 | Walker et al. |
| 7,699,776 B2 | 4/2010 | Walker et al. |

(Continued)

FOREIGN PATENT DOCUMENTS

WO  WO-2011035162 A1  3/2011

OTHER PUBLICATIONS

Nightingale et al., "On the feasibility of remote palpation using acoustic radiation force", J. Acoust. SOC. Am. 110(1), Jul. 2001, 625-634.*

(Continued)

*Primary Examiner* — Phuong Huynh
(74) *Attorney, Agent, or Firm* — Schwegman, Lundberg & Woessner, P.A.

(57) ABSTRACT

Techniques (e.g., system, apparatus, method, machine-readable medium) can be configured for characterizing a rheological or other structural physical property of a sample of a substance. In an example, this can include acoustically bidirectionally deforming the portion of the sample over a deformation range about a neutral-deformation locus within the deformation range, measuring a deformation response of at least a portion of the sample to the insonification, and characterizing the physical property of the sample using the measured response of at least a portion of the sample to the insonification, even in the presence of a flowing substance.

25 Claims, 6 Drawing Sheets

(56) References Cited

U.S. PATENT DOCUMENTS

| | | | |
|---|---|---|---|
| 7,713,201 B2 | 5/2010 | Chen et al. | |
| 7,750,537 B2 | 7/2010 | Hossack et al. | |
| 2003/0013958 A1 | 1/2003 | Govari et al. | |
| 2003/0105398 A1 | 6/2003 | Vitek | |
| 2005/0004463 A1 | 1/2005 | Chen et al. | |
| 2005/0015001 A1 | 1/2005 | Lec et al. | |
| 2005/0148899 A1* | 7/2005 | Walker et al. | 600/553 |
| 2005/0154303 A1 | 7/2005 | Walker et al. | |
| 2006/0052697 A1 | 3/2006 | Hossack et al. | |
| 2006/0100516 A1 | 5/2006 | Hossack et al. | |
| 2007/0016022 A1 | 1/2007 | Blalock et al. | |
| 2007/0016044 A1 | 1/2007 | Blalock et al. | |
| 2008/0091678 A1 | 4/2008 | Walker et al. | |
| 2008/0249408 A1 | 10/2008 | Palmeri et al. | |
| 2008/0302187 A1 | 12/2008 | Huber et al. | |
| 2009/0048519 A1 | 2/2009 | Hossack et al. | |
| 2009/0299184 A1 | 12/2009 | Walker et al. | |
| 2010/0063399 A1 | 3/2010 | Walker et al. | |
| 2010/0138163 A1 | 6/2010 | Gallippi et al. | |
| 2010/0142781 A1 | 6/2010 | Walker et al. | |
| 2010/0168578 A1 | 7/2010 | Garson, Jr. | |
| 2010/0268086 A1 | 10/2010 | Walker et al. | |

OTHER PUBLICATIONS

Liang Zhai et al., "An Integrated Indenter-ARFI Imaging System for Tissue Stiffness Quantification", Ultrason Imaging. Apr. 2008; 30(2): 95-111.*

"European Application Serial No. 10817919.3, Voluntary Amendments filed on Apr. 17, 2012", 14 pgs.

"International Applicaiton Serial No. PCT/US2010/049342, International Preliminary Report on Patentability mailed Mar. 29, 2012", 13 pgs.

"International Application Serial No. PCT/US2010/049342, Search Report mailed Nov. 16, 2010", 4 pgs.

"International Application U.S. Appl. No. PCT/US2010/049342, Written Opinion mailed 11-162010", 16 pgs.

Hsu, Stephen J, et al., "Challenges and Implementation of Radiation-Force Imaging with an Intracardiac Ultrasound Transducer", ieee transactions on ultrasonics, ferroelectrics, and frequency control, vol. 54, No. 5, May 2007, 996-1009.

Nightingale, et al., "Acoustic Radiation Force Impluse Imagin, In Vivo Demonstration of Clinical Feasibility", Ultrasound in Medicine & Biology, Preprint submitted to Ultrasound in Medicine and Biology, (Oct. 24, 2001), 21 pgs.

Nightingale, K R, et al., "Generation and Detection of Acoustic Streaming to Differentiate Between Solid and Cystic Breast Lesions", 1994 Ultrasonic Symposium, 1653-1656.

Nightingale, Kathryn R, et al., "A Finite Element Model of Remote Palpation of Breast Lesions Using Radiation Force: Factors Affecting Tissue Displacement", Ultrasonic Imaging 22, 35-54 (2000), (2000), 35-54.

Nightingale, Kathryn, et al., "Acoustic Radiation Force Impulse Imaging: Remote Palpation of the Mechanical Properties of Tissue", 2002 IEEE Ultrasonics Symposium, (2002), 1821-1830.

Nightingale, Kathryn R, et al., "On the feasibility of remote palpation using acoustic radiation force", J. Acoust. Soc. Am. 110 (1), Jul. 2001, 625-634.

Nightingale, Kathryn, et al., "Shear-Wave Generation Using Acoustic Radiation Force: in Vivo and Ex Vivo Results", Ultrasound in Med. & Biol., vol. 29, No. 12, pp. 1715-1723, 2003, (2003), 1715-1723.

Palmeri, Mark L, et al., "A Finite-Element Method Model of Soft Tissue Response to Impulsive Acoustic Radiation Force", IEEE Transactions on Ultrasonics, Ferroele(JTRICS, and Frequency Control, vol. 52, No. 10, Oct. 2005, 1699-1712.

Palmeri, Mark L, et al., "Ultrasonic Tracking of Acoustic Radiation Force-Induced Displacements in Homogeneous Media", ieee transactions on ultrasonics, ferroelectrics, and frequency control, vol. 53, No. 7, Jul. 2006, 1300-1313.

Tabilo-Munizaga, Gipsy, et al., "Rheology for the food industry", Journal of Food Engineering 67, (2005), 147-156.

Zhai, Liang, et al., "An Integrated Indenter-ARFI Imaging System for Tissue Stiffness Quantification", Ultrason Imaging. Apr. 2008; 30(2): 95-111., (2008), 24 pgs.

* cited by examiner

TRANSDUCER 1

FIG. 3A

TRANSDUCER 2

TRANSDUCER 1

FIG. 3D

TRANSDUCER 2

METHODS, APPARATUS, OR SYSTEMS FOR CHARACTERIZING PHYSICAL PROPERTY IN NON-BIOMATERIAL OR BIO-MATERIAL

CLAIM OF PRIORITY

1. This patent application claims the benefit of priority, under 35 U.S.C. Section 119(e), to William F. Walker et al. U.S. Provisional Patent Application Ser. No. 61/258,949, entitled "METHODS, APPARATUS AND SYSTEMS FOR CHARACTERIZING CHANGES IN NON-BIOMATERIAL AND/OR BIOMATERIAL," filed on Nov. 6, 2009, which is hereby incorporated by reference herein in its entirety.

2. This patent application claims the benefit of priority, under 35 U.S.C. Section 119(e), to William F. Walker et al. U.S. Provisional Patent Application Ser. No. 61/286,605, entitled "METHODS, APPARATUS AND SYSTEMS FOR CHARACTERIZING CHANGES IN NON-BIOMATERIAL AND/OR BIOMATERIAL," filed on Dec. 15, 2009, which is hereby incorporated by reference herein in its entirety.

CROSS-REFERENCE TO RELATED PATENT DOCUMENTS

1. The present application is related to U.S. application Ser. No. 10/971,178, (Publication No. US 2005/0148899 A1) Walker, et al., entitled "Method and Apparatus for Characterization of Clot Formation," filed Oct. 22, 2004, which claims priority from U.S. Provisional Application Ser. No. 60/513,264, filed Oct. 22, 2003," each of which is incorporated by reference herein in its entirety.

2. The present application is related to U.S. application Ser. No. 12/467,216, Walker, et al., entitled "Reduction of Echo Decorrelation Facilitating Motion Estimation," filed May 15, 2009; which claims priority from U.S. Provisional Application Ser. No. 61/053,418, filed May 15, 2008," each of which is incorporated by reference herein in its entirety.

3. The present application is related to PCT Application No. PCT/US2010/049342, Walker et al., entitled ULTRASOUND-BASED METHOD AND RELATED SYSTEM TO EVALUATE HEMOSTATIC FUNCTION OF WHOLE BLOOD, filed on Sep. 17, 2010, which is incorporated by reference herein in its entirety.

STATEMENT REGARDING FEDERALLY SPONSORED RESEARCH OR DEVELOPMENT

This invention was made with government support under award number NIH RO1 EB005433 from National Institute of Health (NIH). The government has certain rights in the invention.

BACKGROUND

The present inventors have recognized that industrial processes can benefit from monitoring of a physical property of a sample of substance being processed. For example, Gipsy Tabilo-Munizaga et al., "Rheology for the Food Industry," J. Food Eng'g. 67 (2005) 147-156, which is incorporated by reference herein in its entirety, discusses rheological measurements for intermediate products during manufacturing and for finished foods. This discussion pertains to large-strain testing that involves deforming a sample to the point of permanent structural change, and small-strain testing that involves less deformation. The commercial rheometers described in Tabilo-Munizaga et al. appear to require insertion of a motor-driven rotor into the substance being processed.

Walker et al. U.S. Patent Application Publication US 2005/0148899 A1, entitled METHOD AND APPARATUS OF CLOT FORMATION, filed on Oct. 22, 2004 and published on Jul. 7, 2005, which is incorporated herein by reference in its entirety, discusses characterizing changes in at least on physical property of soft tissue. Acoustic pulses induce physical displacement of the tissue. Reflected waves are measured to estimate at least one characteristic of the physical displacement induced thereby, such as over time. Physical displacement of blood is measured to estimate at least one characteristic of the physical displacement induced thereby.

Walker et al. U.S. Pat. No. 6,039,691, entitled KINETIC ACOUSTIC OCULAR EXAMINATION APPARATUS AND METHOD, filed on May 29, 1998, and issued on Mar. 21, 2000, which is incorporated herein by reference in its entirety, discusses using ultrasound echo such as to examine the properties of a subject's vitreous body and thus to evaluate or diagnose ocular disorders, such as vitreous traction.

Gallippi et al. U.S. Patent Application Publication US 2010/0138163 A1, entitled METHODS, SYSTEMS, AND COMPUTER READABLE MEDIA FOR MONITORED APPLICATION OF MECHANICAL FORCE TO SAMPLES USING ACOUSTIC ENERGY AND MECHANICAL PARAMETER VALUE EXTRACTION USING MECHANICAL RESPONSE MODELS, filed on Oct. 18, 2009 and published on Jun. 10, 2010, includes a method for determining mechanical property parameters of a sample. Acoustic energy is used to apply a mechanical force to the sample. A measured response or recovery response can be used to determine a value for a first mechanical property parameter of the sample.

OVERVIEW

The present inventors have recognized that industrial processes can benefit from monitoring of a physical property of a sample of substance being processed, such as an elastic, a viscous, or a viscoelastic substance, for example. In particular, the present inventors have recognized that it would be helpful to perform such monitoring without requiring insertion of a rotor into the substance being processed. Instead, the present inventors have recognized that ultrasound techniques can be used, such that contact with the substance being processed is not required. However, the present inventors have recognized that applying such ultrasound techniques to an industrial process that can involve a substantial flow of the substance being processed. The present inventors have recognized that this can present substantial challenges beyond those challenges that present in merely using ultrasound to measure the flow, and beyond those challenges that are present in using ultrasound to measure a physical property (other than flow) in the absence of flow.

For example, the present inventors have recognized that a problem to be solved can include determining an ultrasound-induced or other acoustically-induced physical deformation of a flowing substance. Under such circumstances, the magnitude of the acoustically-induced deformation can be overwhelmed by a much larger bulk displacement arising from the flow of the substance, such as in a food manufacturing or other industrial process. Also, the present inventors have recognized that measuring an acoustically-induced physical deformation of a substance by unidirectionally insonifying the substance can result in an induced non-linearity in the measured response, such as due to the single-direction insonification. Thus, the present inventors have recognized that there is a need for improved techniques for measuring an acoustically-induced physical deformation of a substance, such as when the substance is flowing, or even otherwise.

Example 1 can include subject matter that can include an apparatus for characterizing a physical property of a sample, the apparatus comprising: a first acoustic transducer, configured to insonify a portion of the sample in a first direction; a second acoustic transducer, configured to insonify the portion of the sample in a second direction; a processor circuit, coupled to the first and second acoustic transducers, the processor circuit configured to control operation of the first and second transducers to be capable of acoustically bidirectionally deforming the portion of the sample over a deformation range about a neutral-deformation locus within the deformation range; a deformation response sensor, coupled to the processor circuit, the response sensor configured to measure a deformation response of at least a portion of the sample to the insonification; and wherein the processor circuit is configured to provide an indication characterizing the physical property of the sample using the measured response of at least a portion of the sample to the insonification.

In Example 2, the subject matter of Example 1 can optionally be configured such that the response sensor includes at least one of the first and second acoustic transducers.

In Example 3, the subject matter of any one of Examples 1-2, can optionally be configured such that the processor circuit is configured to vary at least one parameter of the insonification provided by at least one of the first and second acoustic transducers, and to control the response sensor to measure multiple deformation responses of the at least a portion of the sample to respective different variations of the insonification to provide an indication of a physical property of the sample.

In Example 4, the subject matter of any one of Examples 1-3 can optionally be configured such that the processor circuit includes an insonification mode that includes at least one of: a sinusoidal envelope insonification mode, a Gaussian envelope insonification mode, an impulse function insonification mode, a pseudo-random insonification mode, or an arbitrarily-specifiable insonification mode.

In Example 5, the subject matter of any one of Examples 1-4 can optionally be configured such that the processor circuit includes an insonification mode that is capable of being switched between at least two of: a sinusoidal envelope insonification mode, a Gaussian envelope insonification mode, an impulse function insonification mode, a pseudo-random insonification mode, or an arbitrarily-specifiable insonification mode.

In Example 6, the subject matter of any one of Examples 1-5 can optionally be configured such that at least one of the first and second acoustic transducers includes a plurality of insonifying transducers configured to together produce a beat response, and wherein the response sensor is configured to detect the beat response.

In Example 7, the subject matter of any one of Examples 1-6 can optionally be configured such that the processor circuit is configured to control operation of the first and second transducers to be capable of acoustically bidirectionally deforming an acoustically-reflective barrier that is mechanically coupled with the sample.

In Example 8, the subject matter of any one of Examples 1-7 can optionally be configured such that the barrier includes at least one of a membrane positioned against the sample, a meniscus of the sample, or a surface of a vessel carrying the sample.

In Example 9, the subject matter of any one of Examples 1-8 can optionally be configured such that the sample includes a first flowable substance and the membrane includes a second flowable substance having greater acoustic reflectivity than the first flowable substance.

In Example 10, the subject matter of any one of Examples 1-9 can optionally be configured such that the response sensor is configured to measure a strain response of at least a portion of the sample to the insonification, and wherein the processor circuit is configured to control operation of the first and second transducers to provide an adjustable force that maintains a specified strain as measured by the response sensor in the portion of the sample over a period of time.

In Example 11, the subject matter of any one of Examples 1-10 can optionally be configured such that the response sensor is configured to measure a strain response of at least a portion of the sample to the insonification during a period of time wherein the processor circuit is configured to control operation of the first and second transducers to provide a specified fixed force.

In Example 12, the subject matter of any one of Examples 1-11 can optionally be configured such that the response sensor is configured to measure a strain response of at least a portion of the sample to the insonification during a period of time wherein the processor circuit is configured to control operation of the first and second transducers to provide a specified adjustably variable force.

In Example 13, the subject matter of any one of Examples 1-12 can optionally be configured such that the first and second acoustic transducers are configured such that the first and second directions are coaxially opposite.

In Example 14, the subject matter of any one of Examples 1-13 can optionally be configured such that the first and second acoustic transducers are configured such that the first and second directions are opposite and at least one of physically or programmably laterally offset from each other by a specified amount.

In Example 15, the subject matter of any one of Examples 1-14 can optionally be configured such that the first acoustic transducers is configured to produce a first region of insonification in the sample, the second acoustic transducer is configured to provide a second region of insonification in the sample, and wherein the first and second regions of insonification are at least partially overlapping.

In Example 16, the subject matter of any one of Examples 1-15 can optionally be configured such that the first acoustic transducer is configured to produce a first region of insonification in the sample, the second acoustic transducer is configured to provide a second region of insonification in the sample, and wherein respective foci of the first and second regions of insonification are offset from each other.

In Example 17, the subject matter of any one of Examples 1-16 can optionally be configured such that the sample is configured to flow within a vessel at a flow rate that exceeds a physical deformation rate of acoustically deforming the portion of the sample in the direction of flow of the sample.

In Example 18, the subject matter of any one of Examples 1-17 can optionally be configured to measure flow of the sample and at least one of an elastic modulus, a shear modulus, a viscoelastic creep, a viscosity, a storage modulus, a loss modulus, a loss factor, a yield stress, a stress relaxation time constant, a strain relaxation time constant, a fatigue time, or a strain.

In Example 19, the subject matter of any one of Examples 1-18 can optionally be configured such that the physical property of the sample includes at least one of an elastic modulus, a shear modulus, a viscoelastic creep, a viscosity, a storage modulus, a loss modulus, a loss factor, a yield stress, a stress relaxation time constant, a strain relaxation time constant, a fatigue time, or a strain.

In Example 20, the subject matter of any one of Examples 1-19 can optionally further comprise a plurality of acoustic scattering elements included within the sample.

In Example 21, the subject matter of any one of Examples 1-20 can optionally be configure to include acoustic scattering elements that are non-toxic.

In Example 22, the subject matter of any one of Examples 1-20 can optionally be configured such that the indication characterizing the physical property of the sample using the measured response of at least a portion of the sample to the insonification is used to provide closed-loop control of a physical process affecting the physical property of the sample Example 23 can include, or can be combined with the subject matter of any one of Examples 1-22 to optionally include subject matter that can include an apparatus for characterizing a physical property of a sample, the apparatus comprising: a first acoustic transducer, configured to insonify a portion of the sample in a first direction; a second acoustic transducer, configured to insonify the portion of the sample in a second direction that is opposite from the first direction; a processor circuit, coupled to the first and second acoustic transducers, the processor circuit configured to control operation of the first and second transducers to be capable of acoustically bidirectionally deforming the portion of the sample over a deformation range about a neutral-deformation locus within the deformation range; a deformation response sensor, coupled to the processor circuit, the response sensor including at least one of the first and second acoustic transducers and configured to measure a deformation response of at least a portion of the sample to the insonification; wherein the processor circuit is configured to vary at least one parameter of the insonification provided by at least one of the first and second acoustic transducers, and to control the response sensor to measure multiple deformation responses of the at least a portion of the sample to respective different variations of the insonification to provide an indication of a physical property of the sample; and wherein the processor circuit is configured to control operation of the first and second transducers to be capable of acoustically bidirectionally deforming an acoustically-reflective barrier that is mechanically coupled with the sample, wherein the barrier includes at least one of a membrane positioned against the sample, a meniscus of the sample, or a surface of a vessel carrying the sample; and wherein the sample is configured to flow within a vessel at a flow rate that exceeds a physical deformation rate of acoustically deforming the portion of the sample in the direction of flow of the sample.

Example 24 can optionally be combined with the subject matter of any one of Examples 1-23 to include a plurality of non-toxic acoustic scattering elements included within the sample.

Example 25 can include, or can be combined with the subject matter of any one of Examples 1-24 to include, subject matter that can include a method comprising: insonifying a portion of the sample in a first direction; insonifying the portion of the sample in a second direction; controlling insonification to be capable of acoustically bidirectionally deforming the portion of the sample over a deformation range about a neutral-deformation locus within the deformation range; measuring a deformation response of at least a portion of the sample to the insonification; and providing an indication characterizing the physical property of the sample using the measured response of at least a portion of the sample to the insonification.

In Example 26, the subject matter of any one of Examples 1-25 can optionally include using a response sensor that includes at least one of the first and second acoustic transducers.

In Example 27, the subject matter of any one of Examples 1-26, can optionally comprise varying at least one parameter of the insonification provided by at least one of the first and second acoustic transducers, measuring multiple deformation responses of the at least a portion of the sample to respective different variations of the insonification to provide an indication of a physical property of the sample.

In Example 28, the subject matter of any one of Examples 1-27 can optionally include insonifying using an insonification mode that includes at least one of: a sinusoidal envelope insonification mode, a Gaussian envelope insonification mode, an impulse function insonification mode, a pseudo-random insonification mode, or an arbitrarily-specifiable insonification mode.

In Example 29, the subject matter of any one of Examples 1-28 can optionally include using an insonification mode that is capable of being switched between at least two of: a sinusoidal envelope insonification mode, a Gaussian envelope insonification mode, an impulse function insonification mode, a pseudo-random insonification mode, or an arbitrarily-specifiable insonification mode.

In Example 30, the subject matter of any one of Examples 1-29 can optionally include insonifying to produce a beat response, and detecting the beat response.

In Example 31, the subject matter of any one of Examples 1-30 can optionally include acoustically bidirectionally deforming an acoustically-reflective barrier that is mechanically coupled with the sample.

In Example 32, the subject matter of any one of Examples 1-31 can optionally include using a barrier that includes at least one of a membrane positioned against the sample, a meniscus of the sample, or a surface of a vessel carrying the sample.

In Example 33, the subject matter of any one of Examples 1-32 can optionally include using a barrier that includes a first flowable substance and the membrane includes a second flowable substance having greater acoustic reflectivity than the first flowable substance.

In Example 34, the subject matter of any one of Examples 1-33 can optionally include measuring a strain response of at least a portion of the sample to the insonification, and providing an adjustable force that maintains a specified strain as measured by the response sensor in the portion of the sample over a period of time.

In Example 35, the subject matter of any one of Examples 1-34 can optionally include measuring a strain response of at least a portion of the sample to the insonification during a period of time while providing a specified fixed force.

In Example 36, the subject matter of any one of Examples 1-35 can optionally include measuring a strain response of at least a portion of the sample to the insonification during a period of time while providing a specified adjustably variable force.

In Example 37, the subject matter of any one of Examples 1-36 can optionally include coaxially opposite insonifying.

In Example 38, the subject matter of any one of Examples 1-37 can optionally include laterally offset opposite insonifying.

In Example 39, the subject matter of any one of Examples 1-38 can optionally include producing a first region of insonification in the sample, producing a second region of insonification in the sample, and wherein the first and second regions of insonification are at least partially overlapping.

In Example 40, the subject matter of any one of Examples 1-39 can optionally include producing a first region of insonification in the sample, producing a second region of insonification in the sample, and wherein respective foci of the first and second regions of insonification are offset from each other.

In Example 41, the subject matter of any one of Examples 1-40 can optionally include providing flow within a vessel at a flow rate that exceeds a physical deformation rate of acoustically deforming the portion of the sample in the direction of flow of the sample.

In Example 42, the subject matter of any one of Examples 1-41 can optionally include measuring flow of the sample and at least one of an elastic modulus, a shear modulus, a viscoelastic creep, a viscosity, a storage modulus, a loss modulus, a loss factor, a yield stress, a stress relaxation time constant, a strain relaxation time constant, a fatigue time, or a strain.

In Example 43, the subject matter of any one of Examples 1-42 can optionally include determining at least one of an elastic modulus, a shear modulus, a viscoelastic creep, a viscosity, a storage modulus, a loss modulus, a loss factor, a yield stress, a stress relaxation time constant, a strain relaxation time constant, a fatigue time, or a strain.

In Example 44, the subject matter of any one of Examples 1-43 can optionally further comprise using a plurality of acoustic scattering elements included within the sample.

In Example 45, the subject matter of any one of Examples 1-44 can optionally include using acoustic scattering elements that are non-toxic.

In Example 46, the subject matter of any one of Examples 1-45 can optionally include using the measured response of at least a portion of the sample to the insonification is used to provide closed-loop control of a physical process affecting the physical property of the sample These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, an apparatus that can be configured for characterizing a rheological or other structural physical property of a sample of a substance (e.g., a biomaterial, a non-biomaterial, a polymer, a bio-polymer, a plastic, a gel, a sol-gel, glass, cement, an intermediate or finished foodstuff, or other material). This can be accomplished such as by acoustically bidirectionally deforming the portion of the sample over a deformation range about a neutral-deformation locus within the deformation range, measuring a deformation response of at least a portion of the sample to the insonification, and characterizing the physical property of the sample using the measured response of at least a portion of the sample to the insonification, even in the presence of a flowing substance.

Figure 1:
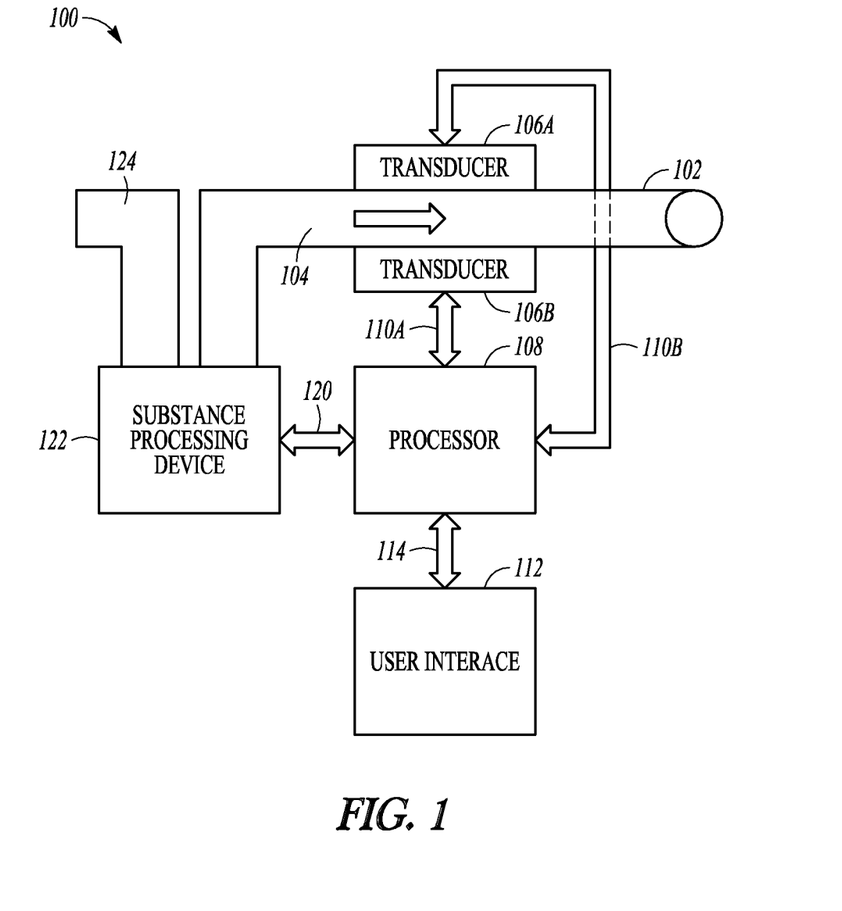
FIG. 1 shows an example of portions of an apparatus that can be used for characterizing a physical property of a sample, and portions of an environment in which it can be used.

FIG. 1 shows an example of portions of an apparatus 100 that can be used for characterizing a physical property of a sample, and portions of an environment in which it can be used. In an example, the environment can include a food manufacturing or other industrial process setting. In an example, a pipe, tube, cuvette, tank, vat, or other vessel 102 can be configured to carry an intermediate or finished food product or other substance 104. In an example, the substance 104 can be capable of flowing within the vessel 102. Such flow can be represented by the directional arrow in FIG. 1. Such flow can be induced by a pressurized source, a pump, gravity, surface tension wicking, or any other flow-inducing technique. In an example, the vessel can also be configured to implement one or more other processing techniques, such as mixing, heating, cooling, curing, or other desired technique for processing the substance.

In an example, the apparatus 100 can include a piezoelectric or other (e.g., optoacoustic, thermoacoustic, etc.) ultrasound or other first acoustic transducer 106A and a piezoelectric or other ultrasound or other second acoustic transducer 106B. Although FIG. 1 shows multiple acoustic transducers 106A-B, which can provide certain advantages as explained herein, in certain examples, a single acoustic transducer can be used, such as, for example, to combine one or more techniques in the patent documents incorporated by reference herein with one or more techniques specifically described herein. In an illustrative example, the first and second acoustic transducers 106A-B can be located across from each other on opposing sides of the vessel 102. The first or second acoustic transducers 106A-B can be affixed or otherwise acoustically or mechanically coupled to the vessel 102, such as to be capable of transmitting acoustic energy to the substance 104 within the vessel. In an example, such acoustic or mechanical coupling to the vessel 102 can allow the first or second acoustic transducers to be capable of acting as a response sensor such as by "listening" for a responsive echo of acoustic energy from the substance 104 within the vessel. However, a separate acoustic transducer or other response sensor can be used, if desired. In an example, a flowing or other sample of the substance 104 can be located between the first and second acoustic transducers 106A-B. A phase-shift or change in arrival time in the responsive echo from the insonified portion of the sample of the substance 104 can be used to indicate a degree of deformation of the substance. A displacement resulting from the acoustically-induced deformation of the substance can phase-shift or alter an arrival time of the resulting echo. The amount of the phase-shift or change in arrival time can indicate the degree of acoustically-induced deformation of the substance. This information, in turn, can be used to characterize a physical property of the substance.

The apparatus 100 can include a processor circuit 108, such as a microprocessor, a microcontroller, computer, hardware state machine, or the like. The processor 108 can include a tangible or other processor-readable medium. The processor-readable medium can be capable of storing instructions that can be executed by the processor 108. This can allow the processor 108 to perform one or more of the techniques described or incorporated herein. A bus 110 can couple the processor 108 to one or both of the first and second transducers 106A-B. The bus 110 can be used to communicate one or more control signals from the processor 108 to one or both of the first or second transducers 106A-B. Such control signals can be used to control insonification timing, modulation or carrier pulse shape, pulse repetition rate, duty-cycle, ultrasound carrier frequency, carrier or modulation amplitude, or the like. The bus 110 can also be used to communicate one or more echo or other response signals. Such response signals can be obtained in response to the insonification, such as from one or both of the first and second transducers 106A-B, and communicated to the processor 108. The processor 108 can then perform signal processing on the response signals. Such signal processing can be used to determine a physical property of at least a portion of the sample of the substance in the vessel 102. In an example, the processor 108 can be coupled to a local or remote computer display monitor or other user interface device, 112, such as by a bus 114. The processor 108 can communicate an indication of the determined physical property of the portion of the sample of the substance 104 in the vessel 102, such as to the user interface device 112, or to another automated device or process.

In an example, an arrangement such as shown in FIG. 1 can allow the first and second acoustic transducers 106A-B to insonify the sample from different directions. In an example, these different directions of insonification can be opposite directions. Such opposite directions can be coaxially-aligned or laterally offset. This can include physically or programmably adjusting the first and second acoustic transducers 106A-B to achieve the desired coaxial alignment or offset. In an example, the user can adjust one or more insonification parameters, such as to produce (coaxial or laterally offset) overlapping or offset regions of insonification, as desired.

In an example, the first and second acoustic transducers 106A-B can be coaxially-aligned to provide temporally alternating directly-opposing insonification pulses. This can provide directly opposing acoustic deformation of a portion of a sample of the substance 104. Therefore, the portion of the sample can be bidirectionally acoustically deformed over a deformation range that extends about a neutral-deformation locus within the deformation range, as illustrated conceptually in the deformation displacement vs. force conceptual illustration of FIG. 2A.

Figure 2A:
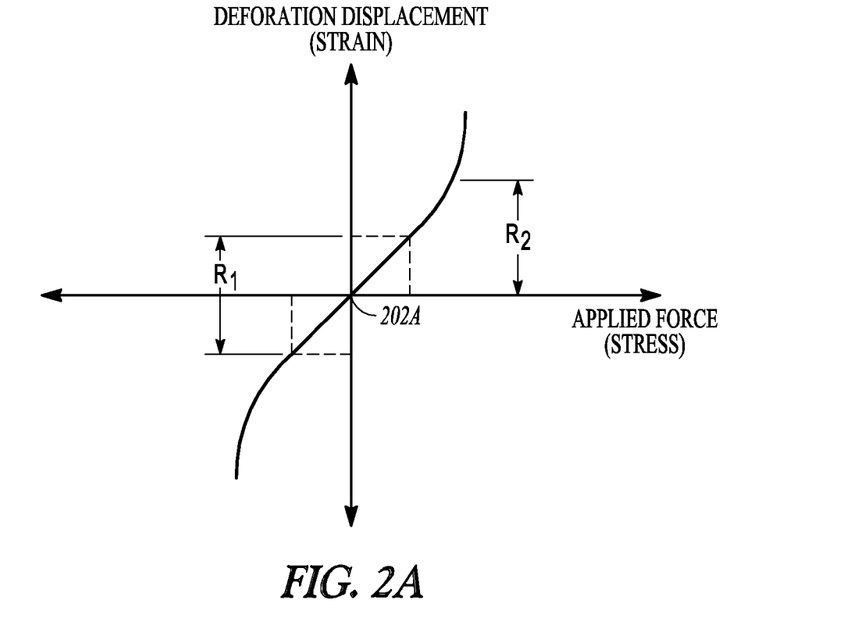
FIG. 2A is an example of a conceptual illustration of deformation displacement vs. applied force in a portion of a sample of a substance.

FIG. 2A is an example of a conceptual illustration of deformation displacement, $\Delta L$, (which can alternatively be represented as strain, $\Delta L/L_0$) vs. applied force (which can alternatively be represented as stress) in a portion of a sample of a substance. In this example, the deformation displacement or strain will exhibit an approximately linear function of applied force or stress over a deformation or strain range $R_1$, such as about a neutral-deformation or neutral-strain locus 202A, which, in this example can correspond to zero force or stress. In the example of FIG. 2A, the deformation displacement or strain can be non-linear with applied force or stress outside of the deformation displacement or strain range $R_1$, such as can be the case in a gel or other viscous substance in which deformation displacement or strain beyond a certain amount can result in onset of flow. In an example, a bidirectional oscillatory acoustic force or stress can be applied (such as using opposing first and second transducers 106A-B) such as can be used to keep the deformation displacement or strain within the linear range $R_1$ or, if desired within a larger range that includes a non-linear portion of the deformation displacement vs. force or strain vs. stress curve. In another example, a unidirectional acoustic force or stress can be applied (such as by using a single transducer 106A), such as can be used to keep the deformation displacement or strain within the positive linear portion of $R_1$, or within a larger positive range $R_2$ that can include a non-linear portion of the deformation displacement vs. applied force or strain vs. stress curve. Using bidirectional oscillatory acoustic applied force or stress can advantageously provide a larger linear operating region of the deformation displacement vs. applied force or strain vs. stress curve, if desired, than a unidirectional acoustic force or stress.

Figure 2B:
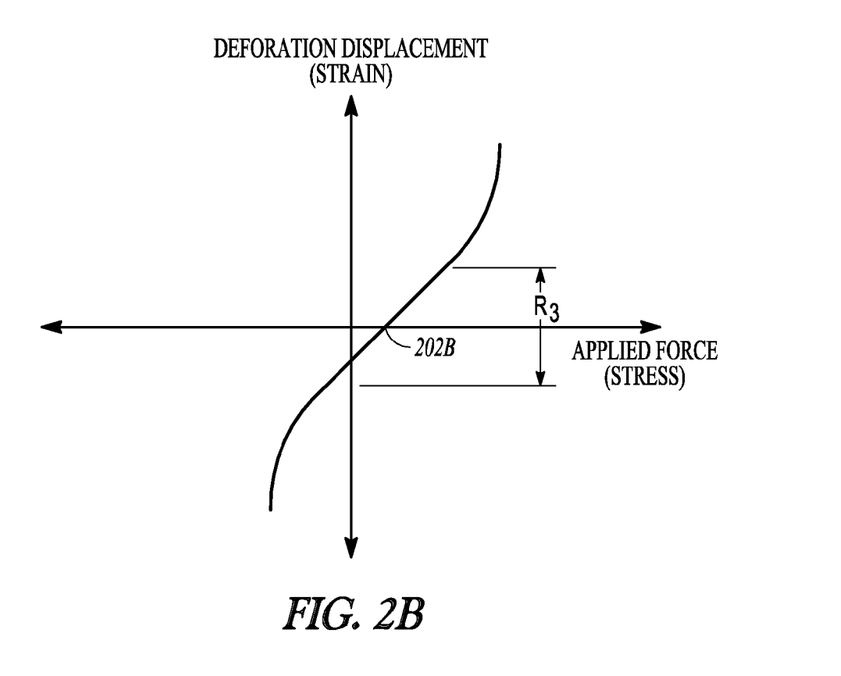
FIG. 2B is an example of a conceptual illustration of deformation displacement vs. applied force in a portion of a sample of a substance, illustrating an example in which a neutral-deformation locus need not correspond to zero-force.

FIG. 2B is an example of a conceptual illustration of deformation displacement, $\Delta L$, (which can alternatively be represented as strain, $\Delta L/L_0$) vs. applied force (which can alternatively be represented as stress) in a portion of a sample of a substance. In this example, the deformation displacement or strain will exhibit an approximately linear function of applied force or stress over a deformation displacement or strain range $R_3$, such as about a neutral-deformation or neutral-strain locus 202B, which, in this example need not correspond to zero force or stress. In the example of FIG. 2B, the deformation displacement or strain can be non-linear with applied force or stress outside of the deformation range $R_3$, such as can be the case in a gel or other viscous substance in which deformation displacement or strain beyond a certain amount can result in onset of flow. As with FIG. 2A, two transducers can be used to provide a bidirectional oscillatory acoustic applied force or stress, with an associated deformation range, or a single transducer can be used to provide a unidirectional acoustic applied force or stress, with an associated deformation range.

In the examples of FIGS. 2A-B or other examples, using bidirectional "oscillatory" deformation displacement or strain about a neutral-deformation or neutral strain locus 202A-B can be advantageous over acoustic deformation from unidirectional insonification. Unidirectional insonification can result in directionally-induced non-linearity or distortion of the neutral-deformation locus (baseline) in the deformation response of the acoustically-deformed portion of the sample, such as relative to an alternatingly-phased bidirectional acoustic deformation of the portion of the sample over a deformation range about a neutral-deformation locus within the deformation range. A unidirectional insonification can also result in a more constrained linear portion of the resulting deformation displacement or strain range. In certain circumstances, this can yield a more accurate acoustic characterization of one or more physical properties of the substance.

Figure 3A:
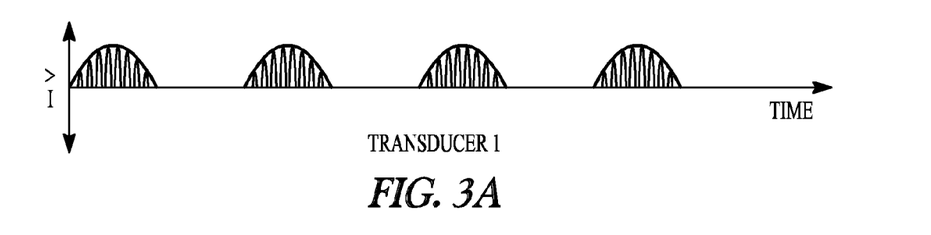
FIGS. 3A-3B are examples of respective acoustic modulation envelope intensity vs. time graphs of first and second transducers such as where positive half-cycle sine wave envelopes of acoustic energy can be delivered.
Figure 3B:
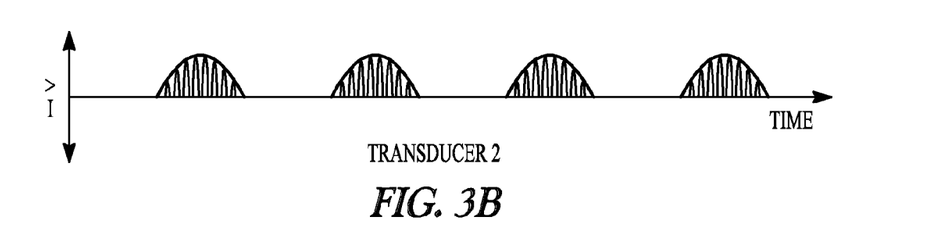

FIGS. 3A-3B are examples of respective acoustic modulation envelope intensity vs. time graphs of the first and second transducers 106A-B, in an example in which positive half-cycle sine wave envelopes of acoustic energy (which, as illustrated, can have a higher carrier frequency, such as in the ultrasound or other desired acoustic frequency range) can be delivered by each of the first and second transducers 106A-B. In the example of FIGS. 3A-B, the positive half-cycle sine wave envelopes can be temporally alternatingly delivered to the first and second transducers 106A-B, respectively. In this way, the first and second transducers can alternatingly insonify a portion of the sample of the substance 104 from different directions, such as from opposite directions. This can create a resulting bidirectional force profile within the portion of the sample, such as shown in the force vs. time graph of FIG. 3C. It is believed that the resulting alternatingly-phased bidirectional acoustic deformation of the portion of the sample over a deformation range about a neutral-deformation locus within a desired deformation range can yield a more accurate acoustic characterization of one or more physical properties of the substance. Such increased accuracy can be particularly beneficial when the substance 104 flows in a large-scale (e.g., bulk) manner such as as in an industrial process. Such bulk flow can induce a significantly larger flow-displacement than the acoustic deformation response. Although an acoustic or other measurement of bulk flow can be made, and used to compensate the acoustic deformation response measurement, the accuracy of the acoustic deformation response measurement can still benefit from other accuracy enhancements, particularly in the presence of such bulk flow.

Figure 3C:
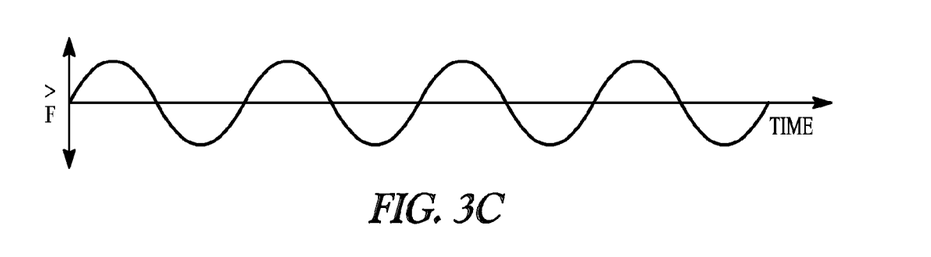
FIG. 3C shows an example of a bidirectional force profile within the portion of a sample, such resulting from the insonification shown in FIGS. 3A-3B.
Figure 3D:
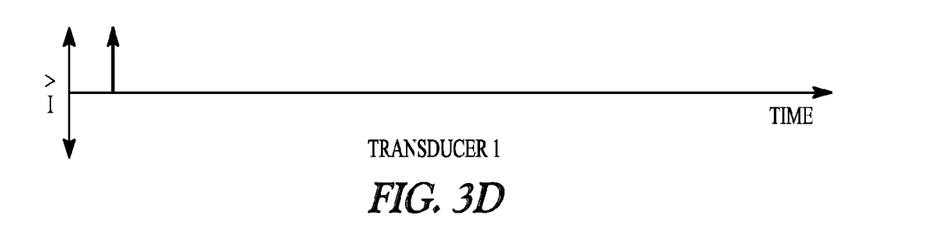
FIGS. 3D-3E are examples of a bidirectional impulse response.
Figure 3E:
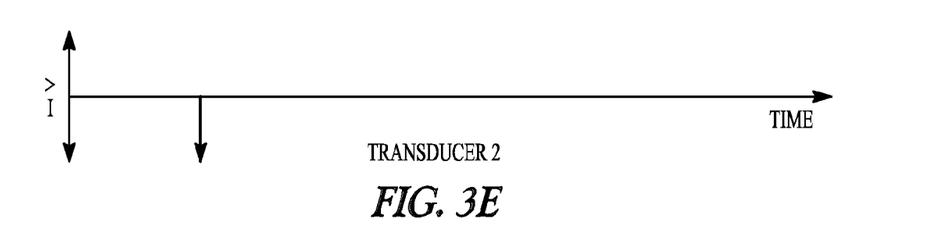

The processor 108 can include a user-programmable, programmable, or otherwise adjustable insonification mode. Examples of different insonification mode types can include, among other things:

1. a bidirectional sinusoidal insonification mode, such as using alternatingly-phased positive half-cycle sine wave acoustic energy modulation envelopes, such as shown in the intensity vs. time illustrations of FIGS. 3A-3C;

2. a bidirectional (e.g., paired) impulse function insonification mode, such as shown in FIGS. 3D-3E;

3. a bidirectional Gaussian insonification mode, such as using alternatingly-phased positive-half cycle Gaussian enveloped sinusoids (e.g., with an ultrasound carrier frequency centered at about 10 MHz);

4. a pseudo-random insonification mode, such as in which pulsed sinusoidal, Gaussian, or other envelopes of acoustic energy are delivered at a pseudo-random pulse repetition rate; or 5. an arbitrarily-specifiable (e.g., user-specifiable) insonification mode. Unidirectional insonification modes can also be included. In an example, the processor 108 can be configured to be capable of being switched between at least two different insonification mode types, such as the between the different examples listed above, between desired combinations of the different examples listed above, or between other insonification mode types. The particular insonification mode will have associated instructions for controlling insonification or listening of the first and second transducers 106A-B, such as according to the desired insonification mode, or in accordance with one or more parameters of the desired insonification mode.

In general, the acoustic intensity experienced by the desired portion of the sample of the substance 104 will depend on, among other things, the effective surface area of the first and second transducers 106A-B, and the particulars of the excitation carrier signal and carrier signal modulation envelope applied to the first and second transducers 106A-B. The resulting applied force experienced by the desired portion of the sample of the substance will be proportional to the acoustic intensity. In an example, the processor circuit 108 can be configured to include instructions for providing the desired excitation carrier signal and carrier signal modulation envelope to the first and second transducers 106A-B, as well as for providing the appropriate signal processing (corresponding to the particular excitation) for determining a resulting phase-shift or change in arrival time of the echo or other response signal that is used to determine the physical property of the portion of the sample of the substance 104. Some illustrative examples of control signal processing and corresponding response signal processing that can be adapted for use in conjunction with the present techniques are described in William F. Walker et al., U.S. Patent Publication No. 2005/01498899, filed Oct. 22, 2004, and published on Jul. 7, 2005, entitled METHOD AND APPARATUS FOR CHARACTERIZATION OF CLOT FORMATION," which is incorporated herein by reference in its entirety, including its description of control signal processing and corresponding response signal processing, including modulation and demodulation techniques.

Figure 4:
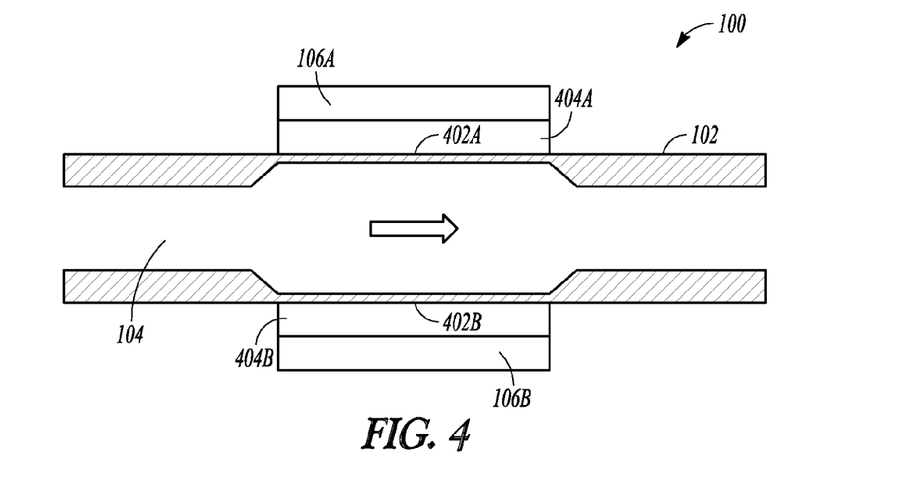
FIG. 4 is an cross-sectional example of portions of an apparatus in which first and second transducers can be acoustically or mechanically coupled to respective acoustically-reflective or other acoustically-deformable barriers.

FIG. 4 is an cross-sectional example of portions of the apparatus 100 in which the first and second transducers 106A-B can be acoustically or mechanically coupled to respective acoustically-reflective or other acoustically-deformable barriers 402A-B, such as by a fluid or other acoustic coupling media 404A-B. An example of such a barrier 402 can include, among other things, a membrane positioned against the sample of the substance 104, a meniscus of the sample, or a surface of a vessel 102 carrying the sample. In the example of FIG. 4, the barrier 402 can be a thinned-down section of the vessel 102. However, this is not required; in an example, the barrier 402 can be the surface of the vessel without such thinning.

In an example, the barrier 402 can be selected or configured so as to provide a desired acoustic impedance relationship to the acoustic coupling media 404A-B that can be acoustically or mechanically coupled thereto as an intermediate component between the acoustic transducer and the barrier 402. In an example, the barrier 402 can be selected or configured to provide an acoustic impedance mismatch between the barrier 402 and the corresponding acoustic coupling media 404A-B, such as to promote reflection of the acoustic energy by the barrier 402. This can help increase or maximize acoustic vibration of the barrier 402. In an example, the barrier 402 can be selected or configured to provide an acoustic resonance of the barrier 402 in response to the acoustic energy provided by the corresponding acoustic transducer. This can help increase or maximize acoustic vibration of the barrier 402.

In an example in which the barrier 402 is designed to vibrate to increase the deformation displacement response of the portion of the sample of the substance 104, if it is desired to detect a phase-shift or change in arrival time of the echo or other response directly from the portion of the sample of the substance 104, a separate response sensor can be used, such that the separate response sensor can be tailored for "listening" to the response from the sample of the substance 104, particularly where the first and second acoustic transducers are configured to increase or maximize acoustic energy input into the sample of the substance 104.

An example of techniques suitable for determining a physical property of a portion of a sample of a substance by sensing a vibratory response of a substance to an acoustically-deformable reflective membrane is described in William F. Walker et al., U.S. Patent Publication No. 2005/01498899, filed Oct. 22, 2004, and published on Jul. 7, 2005, entitled METHOD AND APPARATUS FOR CHARACTERIZATION OF CLOT FORMATION," which is incorporated herein by reference in its entirety, including its sensing a response of a substance to an acoustically-deformable reflective membrane for determining a physical property of a material contacting the membrane.

The above description of FIG. 4 primarily highlighted an example in which the barrier 402 can include a membrane positioned against the sample of the substance 104, wherein the membrane can be acoustically-deformed to induce vibrations, and is held in place but otherwise relatively mechanically unconstrained so as to permit vibrations. A phase-shift or change in arrival time of an echo from the sample can be monitored as a response signal from which a rheological or other structural physical property of the sample can be determined. In an example, a meniscus of the sample itself can be used as the barrier 402, and vibrated, and a phase-shift or change in arrival time of an echo from the sample can be monitored as a response signal from which a rheological or other structural physical property of the sample can be determined. In an example in which the sample forms a first liquid or other flowable layer, an immiscible second liquid or other flowable layer can be be used as the barrier 402 (e.g., oil-on-water, or the like). In an example, the immiscible second layer can be configured to be more acoustically-reflective than the adjacent first flowable layer from which the rheological or other structural physical property of the sample is to be determined. In an example, this can include mixing or floating inert non-toxic acoustic scattering beads or similar elements in or on the immiscible second layer. Some illustrative examples of some acoustic scatterers can include glass microspheres, fumed silica particles, polystyrene beads, graphite beads or powder, or the like. The use of such acoustic scattering elements can enhance the vibration of the barrier, and a phase-shift or change in arrival time of an echo from the sample can be monitored as a response signal from which a rheological or other structural physical property of the sample can be determined. In an example, one or more types of such acoustic scattering elements can optionally be mixed with the sample, if desired, such as to enhance sensitivity of the measured response, wherein the measured response can include a phase-shift or change in arrival time of an echo from the sample can be monitored as a response signal from which a rheological or other structural physical property of the sample can be determined. Where the sample is a substance 104 is an intermediate or finished product in a food process, and intended to be edible, a non-toxic acoustic scattering element can be used. For example, fumed silica is non-toxic and sometimes used as a thickening agent in certain foodstuffs, and can be used as an acoustic scatterer in the present context.

Figure 7A:
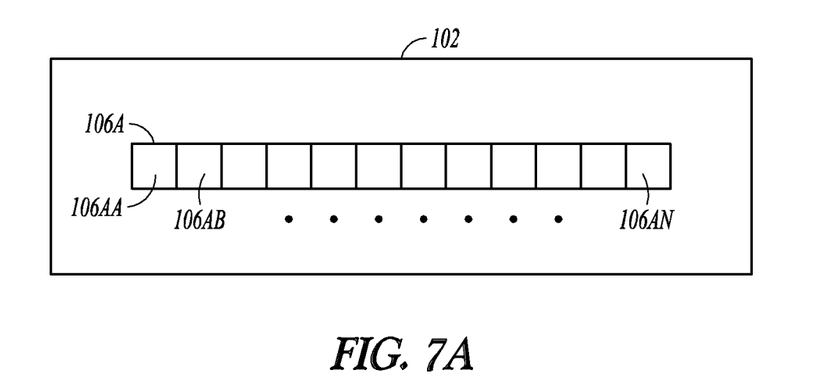
FIG. 7A shows an example that can include a one-dimensional longitudinal array of acoustic transducers, such as in the direction of flow of the substance in a vessel.
Figure 7B:
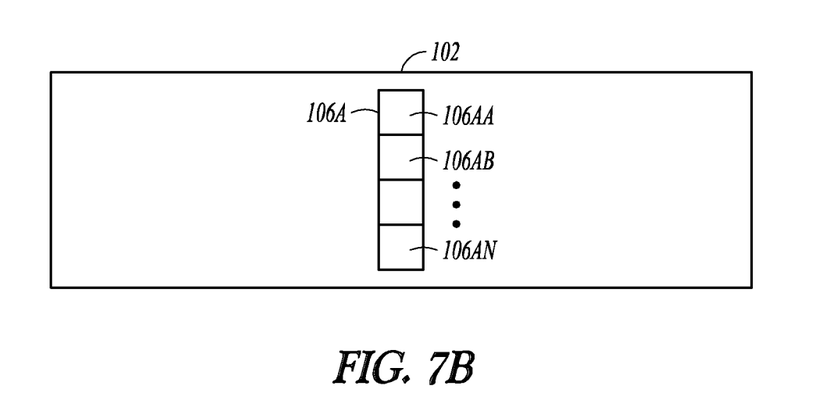
FIG. 7B shows an example that can include a one-dimensional transverse array of acoustic transducers, such as transverse to the direction of flow of the substance in the vessel.
Figure 7C:
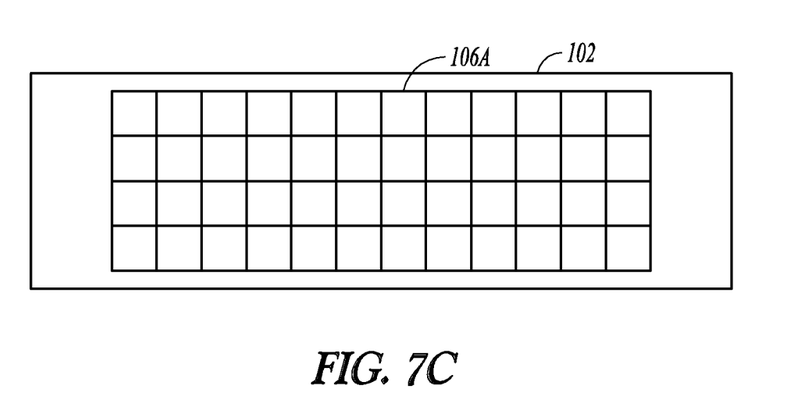
FIG. 7C shows an example that can include a two-dimensional array of acoustic transducers.
Figure 7D:
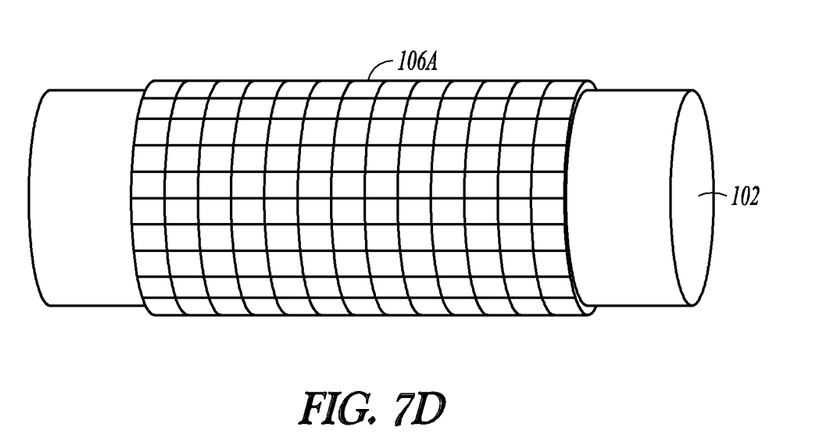
FIG. 7D shows an example of a portion of the apparatus that can include a two-dimensional cylindrical (or semi-cylindrical) array of acoustic transducers.

In an example, the first and second acoustic transducers 106A-B need not be single transducers. Instead, one or both of the first or second transducers 106A-B can include multiple acoustic transducers. In an example, the first and second acoustic transducers 106A-B can include an array of acoustic transducers. For example, by providing a 1-dimensional, 2-dimensional, or 3-dimensional (e.g., annular or cylindrical) array of acoustic transducers 106A-B, the location or direction of insonification or response sensing can be programmably adjusted without physically re-positioning the transducers. This can allow electronic positioning or repositioning of the location of insonification or response sensing at different locations in the direction of flow, lateral thereto, or as otherwise desired. FIG. 7A shows an example of a portion of the apparatus 100 that can include a one-dimensional longitudinal array of acoustic transducers 106AA . . . 106AN, such as in the direction of flow of the substance in the vessel 102. FIG. 7B shows an example of a portion of the apparatus 100 that can include a one-dimensional transverse array of acoustic transducers 106AA . . . 106AN, such as transverse to the direction of flow of the substance in the vessel 102. FIG. 7C shows an example of a portion of the apparatus 100 that can include a two-dimensional array of acoustic transducers. FIG. 7D shows an example of a portion of the apparatus that can include a two-dimensional cylindrical (or semi-cylindrical) array of acoustic transducers.

Figure 5:
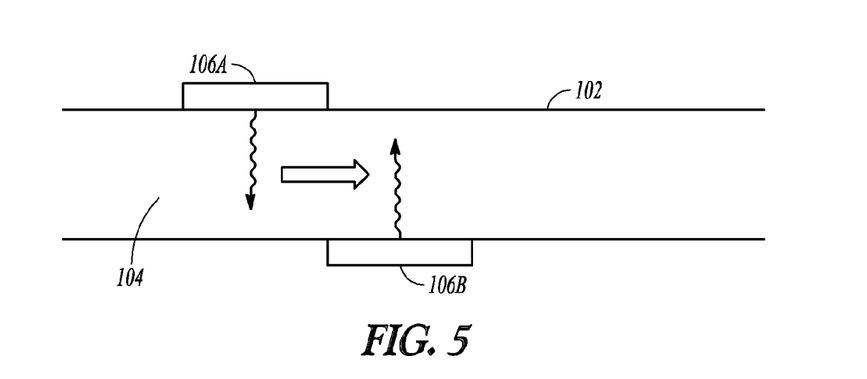
FIG. 5 shows an example in which first and second transducers can be physically or programmably offset from each other in a direction of bulk flow of the substance.

FIG. 5 shows an example in which the first and second transducers 106A-B can be physically or programmably offset from each other in a direction of bulk flow of the substance 104. Offset opposing insonification vectors can be used to create a shear in a portion of the sample of the substance 104, such as where the physical property of the substance 104 to be determined is a shear characteristic of the substance. FIG. 5 shows the first and second transducers 106A-B being offset from each other in a direction of bulk flow of the substance 104. However, in an example, the first and second transducers 106A-B can be physically or programmably laterally offset from each other, such as at the same location along the direction of bulk flow of the substance. Such an arrangement of laterally offset opposing insonification vectors can also be used to perform a shear test or other desired determination of the physical property of the substance. For example, offset orthogonal insonification vectors can be used to create a torsional stress in a portion of the sample of the substance 104, such as where the physical property of the substance 104 to be determined is a torsional stress characteristic of the substance.

In any of the examples discussed herein, the first or second transducers 106A-B need not be dedicated acoustic transducers that are introduced into a food-processing or other industrial application solely for the purpose of measuring a physical property of a substance such as an intermediate or finished product in the process. Instead, the first or second transducers 106A-B can make use of acoustic transducers that already exist in an apparatus associated with the process—such as ultrasound transducers that can be present for imaging or for measuring the bulk flow of the substance 104 through the vessel 102. In an example, the first or second transducers 106A-B can be configured to measure the bulk velocity or flow of the substance 104 in the vessel 102, such as by using Dopper-shift, transit-time, or any other suitable measurement. Moreover, such measurements of bulk velocity or flow of the substance 104 in the vessel from the first or second transducers 106A-B (or from any other measurement device, method, or technique) can be used to calibrate or compensate the measurement of the physical property of the substance 104 obtained using the deformation displacement information described herein.

Figure 6:
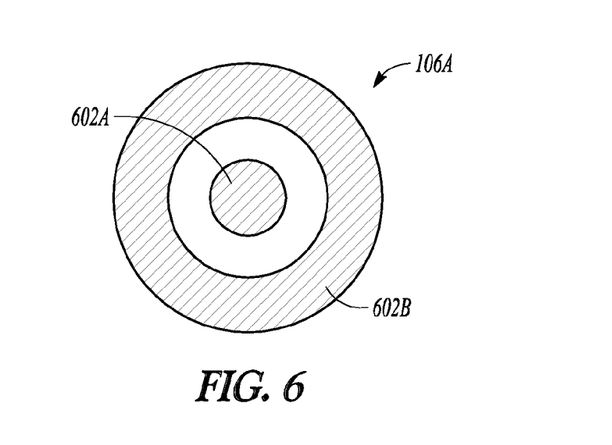
FIG. 6 shows an example in which one or both of first and second transducers can include multiple transducers.

FIG. 6 shows an example in which one or both of the first and second transducers 106A-B can include multiple transducers. In the example shown in FIG. 6, the first transducer 106A (or the second transducer 106B) includes multiple acoustic transducers, such as first transducer 602A and a second transducer 602B that can be positioned with respect to each other to produce a beat response in a portion of the sample of the substance 104 being insonified. In an example, the beat frequency of the beat response can be measured, such as using a vibro-acoustographical technique, and used to determine a rheological or structural physical property of the substance such as stress, strain, modulus, elastic modulus, a shear modulus, a viscoelastic creep, a viscosity, a storage modulus, a loss modulus, a loss factor, a yield stress, a stress relaxation time constant, a strain relaxation time constant, a fatigue time, a Deborah number, a Reynolds number, a dynamic modulus, or other rheological or structural physical property of the substance (as distinct from bulk flow or the like).

The arrangement shown in FIG. 6 is an illustrative example of how insonification can be provided so as to generate a beat frequency response in the desired portion of the sample. Other techniques of providing a confocal or similar arrangement of insonification beams or otherwise generating a beat frequency response can similarly be used in the present context.

Some Examples of Tests for Extracting Rheological or Structural Physical Property of a Substance An ultrasound or other acoustic radiation force per unit volume can be related to the velocity of sound, "c" in the medium or substance of the sample under test, along with the acoustic absorption coefficient of the medium, "α," and a temporal average intensity, "I," at specified spatial locus. For example, a magnitude of a radiation force, "|F|," can be proportional to the absorption coefficient, intensity, and the velocity of sound, such as can be expressed via a relation:

$$|F| \propto \frac{\alpha I}{c} \qquad \text{[EQN. 1]}$$

In an example, such an intensity, propagation velocity, or absorption coefficient can be measured. This can provide an estimate of the radiation force provided by an ultrasonic or other acoustic transducer. For example, an acoustic energy intensity provided by a first acoustic transducer 106A can be measured by a response sensor, such as a second acoustic transducer 106B, such as can be placed a specified distance away from the first acoustic transducer 106A. In an example, in the absence of a sample medium located between the first and second acoustic transducers 106A-B, a first acoustic energy intensity can be measured. Then, a sample can be placed between the first and second acoustic transducers 106A-B, and generally a second (e.g., reduced) acoustic energy intensity can be detected by the second acoustic transducer 106B when the sample is present. A difference between the first and second acoustic energy intensities (which can be normalized by the distance between the first and second acoustic transducers 106A-B), can be proportional to the acoustic absorption coefficient of the medium of the substance 104 (e.g., in units of Nepers/meter).

Similarly, an acoustic velocity of sound can be measured, such as by using a transit time or other desired measurement technique. For example, a pulse or other signal of finite duration can be provided by the first acoustic transducer 106A, and a clock or interval timer can be started concurrently thereto. Then, the pulse or other signal can be detected by a response sensor, such as the second acoustic transducer 106B. The clock or interval timer can be used to provide information about a delay or interval between initiation of transmission of the pulse from the first acoustic transducer 106A and the earliest instant of reception by the second acoustic transducer 106B, or using some other indication of reception of the pulse at the second acoustic transducer 106B, such as can be measured and synchronized with the transmission of the pulse by the first acoustic transducer 106A.

The acoustic energy intensity provided by an ultrasound or other acoustic transducer can be determined, such as using one or a variety of different techniques. Examples can include direct measurement of the acoustic energy intensity by another (e.g., calibrated) ultrasound or other acoustic transducer, or using a thermoacoustic technique, or using a displacement measurement technique, or via one or more other techniques.

In sum, a known acoustic radiation force can be determined and used to insonify a sample of a medium or substance having a known acoustic propagation velocity and attenuation factor (e.g., such as can be determined using one or more techniques above). This information can be used to configure an ultrasonic or other acoustic transducer to provide a calibrated acoustic energy intensity. This, in turn, can be used to determine a rheological or structural physical property of the substance, such as stress, strain, modulus, elastic modulus, a shear modulus, a viscoelastic creep, a viscosity, a storage modulus, a loss modulus, a loss factor, a yield stress, a stress relaxation time constant, a strain relaxation time constant, a fatigue time, a Deborah number, a Reynolds number, a dynamic modulus, or other rheological or structural physical property of the substance (as distinct from bulk flow or the like).

Stress:

In an example, an estimate of stress, "$\hat{\sigma}$," can be determined, such as by using information about an applied body force, "|F|," multiplied by the axial length of the region subjected to the body force, "L." Such a body force can include the radiation force per unit volume, such as can be determined using one or more techniques of the above examples. Such a stress can be represented by $$\hat{\sigma} = |F| \times L \qquad \text{[EQN. 2]}$$

Strain:

An estimate of strain (e.g., a unitless "engineering" strain), "$\hat{\varepsilon}$," can be determined such as using information about a displacement or deformation of a sample, "$\hat{x}$," such as induced by insonification by an ultrasonic or other acoustic transducer, and dividing such a displacement (e.g., in units of length), by an original axial length of the region where a body force is acting, "$L_0$." Such a body force can include the radiation force per unit volume, such as can be determined using one or more techniques of the examples above. Such a strain can be represented by $$\hat{\varepsilon} = \frac{\hat{x}}{L_0} \qquad \text{[EQN. 3]}$$

Modulus:

An elastic modulus (e.g., in Newtons per square meter) can be estimated. This can include determining a first estimated stress corresponding to a first estimated strain, and a second estimated stress corresponding to a second estimated strain. The estimated elastic modulus, "$\hat{E}$," can be determined using the difference between the second and first estimated stresses, "$\sigma_2-\sigma_1$," divided by the difference between the second and first estimated strains, "$\epsilon_2-\epsilon_1$":

$$\hat{E} = \frac{\Delta\sigma}{\Delta\varepsilon} = \frac{\sigma_2-\sigma_1}{\varepsilon_2-\varepsilon_1} \qquad [\text{EQN. 4}]$$

Stress-Relaxation Using Substantially Constant Strain:

In an example, a response sensor can be configured to measure a strain response of at least a portion of a medium or sample to the insonification, in which the processor 108 is configured to perform instructions such as to control operation of the first and second transducers 106A-B to provide an adjustable force that maintains a specified strain as measured by the response sensor in the portion of the sample over a period of time. The applied force vs. time curve can be provided to a user or automated process, or compared to or correlated against a desired (or undesired) template and a result of the comparison or correlation provided to the user or automated process.

Strain-Relaxation or Creep Test:

In an example, a response sensor can be configured to measure a strain response of at least a portion of a medium or sample to the insonification during a period of time wherein the processor 108 is configured to control operation of the first and second transducers 106A-B to provide a specified fixed force. The measured strain response vs. time curve can be provided to a user or automated process, or compared to or correlated against a desired (or undesired) template and a result of the comparison or correlation provided to the user or automated process.

Yield Test:

In an example, a response sensor can be configured to measure a strain response of at least a portion of a medium or sample to the insonification during a period of time wherein the processor 108 is configured to control operation of the first and second transducers 106A-B to provide a specified variable force, such as a linearly ramped or other increasing force. The measured strain response vs. time curve or measured strain response vs. force curve can be provided to a user or automated process, or compared to or correlated against a desired (or undesired) template and a result of the comparison or correlation provided to the user or automated process.

Some Examples of Application Using Closed-Loop Process Control

The above description, such as with respect to FIG. 1, has emphasized measurement of a rheological or other structural physical property of a sample, such as a sample of a substance in a food manufacturing or other industrial process. In an example, such information about the rheological or other structural physical property of a sample can be used to control an process, such as, for example, in a closed-loop manner.

Returning to the example shown in FIG. 1, the processor 108 can be configured as a process controller that can use an indication about the rheological or other structural physical property of a sample can be used to generate a control signal that can be communicated, such as via a bus 120 to a process control actuator of a substance processing device 122. Some examples of the substance processing device 122 can include a mixer, an oven, a cooler, or the like. In an example, the substance processing device 122 can alter a substance processing parameter that can directly or indirectly affect the measured rheological or other structural physical property of the sample, thereby allowing closed-loop feedback control over the process.

For example, material viscoelasticity can be useful in assessing the quality of one or more of a food, a lubricant, an adhesive, and a broad range of industrial products. One or more viscoleastic properties can indicate the quality of a final product or can indicate that a product is not yet complete. The quality of ketchup, for example, can be associated with the viscosity of the final product. The cure of an adhesive can be assessed by the viscoelasticity of that adhesive. The techniques described herein can be used for either monitoring a process, or for actually controlling the process using monitored process information about a rheological or other structural physical property of the sample.

Because viscoleastic properties can be an indicator of quality, or can indicate product completeness, the present inventors have recognized that there is a need to develop a system capable of using information about one or more measured viscoelastic properties as mechanism to control one or more manufacturing processes. Existing methods for measuring viscoelastic properties can be cumbersome, can require using sensitive mechanical parts, can require removing a sample from the manufacturing process, and may not easily be used to control product manufacture in a closed loop manner.

In an example, the present techniques can be directed at a goal of providing improved product manufacturing, such as by allowing rapid and unobtrusive measurement of one or more viscoelastic properties, and using information about such a measurement to assess or control product manufacture. This can involve employing ultrasound radiation force, such as using the techniques described or incorporated herein, such as to measure one or more viscoelastic properties and to apply information obtained from one or more such measurements to guide the manufacturing process. This can allow more rapid manufacture of a variety of products and more precise control of one or more desired properties of the product.

In an example of an application of the present systems, methods, and other techniques, a ketchup manufacturer can produce a more consistent product without the need for human control and input. Instead, ultrasound or other acoustic radiation force based techniques can be used to assess the viscosity of the intermediate or final product. If the viscosity is found to be too low a thickening agent can be added to the product. If the viscosity is found to be too high then a thinning agent can be added. Cure time or temperature can also be adjusted automatically using the measured information. The present techniques can be applied in a fully automated manner to monitor the product and perform the titration, such that human intervention is not required. However, the present techniques can alternatively use human intervention, such as to titrate the thickening agent, thinning agent, to adjust a cure time or temperature, or the like.

In another example of an application, the techniques described or incorporated herein can be used to cook a food product such as gravy. The viscosity measurement component can be used to assess the gravy's viscosity, information about which can be used to automatically control a heater to cook the gravy. When a specified viscosity is achieved, the heater can be adjusted to halt cooking, or the manufacturing can halt and the gravy can be be packaged for cooling and sale.

In yet another example of an application, the techniques described or incorporated herein can be employed to monitor and direct the replacement of motor lubricant. When the viscosity of the lubricant (such as automobile motor oil) falls outside some predetermined range then an operator can be directed to replace the lubricant.

These examples are for illustrative purposes, and are not intended to be limiting, and can use both unidirectional insonification (e.g., using a single transducer) or bidirectional insonification (e.g., using two or more transducers).

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus for characterizing a physical property of a sample, the apparatus comprising:
   a first acoustic transducer, configured to insonify a portion of the sample in a first direction;
   a second acoustic transducer, configured to insonify the portion of the sample in a second direction;
   a processor circuit, coupled to the first and second acoustic transducers, the processor circuit configured to control operation of the first and second transducers to be capable of acoustically bidirectionally deforming the portion of the sample over a deformation range about a neutral-deformation locus within the deformation range;
   a deformation response sensor, coupled to the processor circuit, the response sensor configured to measure a deformation response of at least a portion of the sample to the insonification; and
   wherein the processor circuit is configured to provide an indication characterizing the physical property of the sample using the measured response of at least a portion of the sample to the insonification.

2. The apparatus of claim 1, wherein the response sensor includes at least one of the first and second acoustic transducers.

3. The apparatus of claim 1, wherein the processor circuit is configured to vary at least one parameter of the insonification provided by at least one of the first and second acoustic transducers, and to control the response sensor to measure multiple deformation responses of the at least a portion of the sample to respective different variations of the insonification to provide an indication of a physical property of the sample.

4. The apparatus of claim 1, where the processor circuit includes an insonification mode that includes at least one of: a sinusoidal envelope insonification mode, a Gaussian envelope insonification mode, an impulse function insonification mode, a pseudo-random insonification mode, or an arbitrarily-specifiable insonification mode.

5. The apparatus of claim 1, where the processor circuit includes an insonification mode that is capable of being switched between at least two of: a sinusoidal envelope insonification mode, a Gaussian envelope insonification mode, an impulse function insonification mode, a pseudo-random insonification mode, or an arbitrarily-specifiable insonification mode.

6. The apparatus of claim 1, wherein at least one of the first and second acoustic transducers includes a plurality of insonifying transducers configured to together produce a beat response, and wherein the response sensor is configured to detect the beat response.

7. The apparatus of claim 1, wherein the processor circuit is configured to control operation of the first and second transducers to be capable of acoustically bidirectionally deforming an acoustically-reflective barrier that is mechanically coupled with the sample.

8. The apparatus of claim 7, wherein the barrier includes at least one of a membrane positioned against the sample, a meniscus of the sample, or a surface of a vessel carrying the sample.

9. The apparatus of claim 8, wherein the sample includes a first flowable substance and the membrane includes a second flowable substance having greater acoustic reflectivity than the first flowable substance.

10. The apparatus of claim 1, wherein the response sensor is configured to measure a strain response of at least a portion of the sample to the insonification, and wherein the processor circuit is configured to control operation of the first and second transducers to provide an adjustable force that maintains a specified strain as measured by the response sensor in the portion of the sample over a period of time.

11. The apparatus of claim 1, wherein the response sensor is configured to measure a strain response of at least a portion of the sample to the insonification during a period of time wherein the processor circuit is configured to control operation of the first and second transducers to provide a specified fixed force.

12. The apparatus of claim 1, wherein the response sensor is configured to measure a strain response of at least a portion of the sample to the insonification during a period of time wherein the processor circuit is configured to control operation of the first and second transducers to provide a specified adjustably variable force.

13. The apparatus of claim 1, wherein the first and second acoustic transducers are configured such that the first and second directions are coaxially opposite.

14. The apparatus of claim 1, wherein the first and second acoustic transducers are configured such that the first and second directions are opposite and at least one of physically or programmably laterally offset from each other by a specified amount.

15. The apparatus of claim 1, wherein the first acoustic transducer is configured to produce a first region of insonification in the sample, the second acoustic transducer is configured to provide a second region of insonification in the sample, and wherein the first and second regions of insonification are at least partially overlapping.

16. The apparatus of claim 1, wherein the first acoustic transducer is configured to produce a first region of insonification in the sample, the second acoustic transducer is configured to provide a second region of insonification in the sample, and wherein respective foci of the first and second regions of insonification are offset from each other.

17. The apparatus of claim 1, wherein the sample is configured to flow within a vessel at a flow rate that exceeds a physical deformation rate of acoustically deforming the portion of the sample in the direction of flow of the sample.

18. The apparatus of claim 17, wherein the apparatus is configured to measure flow of the sample and at least one of an elastic modulus, a shear modulus, a viscoelastic creep, a viscosity, a storage modulus, a loss modulus, a loss factor, a yield stress, a stress relaxation time constant, a strain relaxation time constant, a fatigue time, or a strain.

19. The apparatus of claim 1, wherein the physical property of the sample includes at least one of an elastic modulus, a shear modulus, a viscoelastic creep, a viscosity, a storage modulus, a loss modulus, a loss factor, a yield stress, a stress relaxation time constant, a strain relaxation time constant, a fatigue time, or a strain.

20. The apparatus of claim 1, further comprising a plurality of acoustic scattering elements included within the sample.

21. The apparatus of claim 20, wherein the acoustic scattering elements are non-toxic.

22. The apparatus of claim 1, wherein the indication characterizing the physical property of the sample using the measured response of at least a portion of the sample to the insonification is used to provide closed-loop control of a physical process affecting the physical property of the sample.

23. An apparatus for characterizing a physical property of a sample, the apparatus comprising:
   a first acoustic transducer, configured to insonify a portion of the sample in a first direction;
   a second acoustic transducer, configured to insonify the portion of the sample in a second direction that is opposite from the first direction;
   a processor circuit, coupled to the first and second acoustic transducers, the processor circuit configured to control operation of the first and second transducers to be capable of acoustically bidirectionally deforming the portion of the sample over a deformation range about a neutral-deformation locus within the deformation range;
   a deformation response sensor, coupled to the processor circuit, the response sensor including at least one of the first and second acoustic transducers and configured to measure a deformation response of at least a portion of the sample to the insonification;
   wherein the processor circuit is configured to vary at least one parameter of the insonification provided by at least one of the first and second acoustic transducers, and to control the response sensor to measure multiple deformation responses of the at least a portion of the sample to respective different variations of the insonification to provide an indication of a physical property of the sample; and
   wherein the processor circuit is configured to control operation of the first and second transducers to be capable of acoustically bidirectionally deforming an acoustically-reflective barrier that is mechanically coupled with the sample, wherein the barrier includes at least one of a membrane positioned against the sample, a meniscus of the sample, or a surface of a vessel carrying the sample; and
   wherein the sample is configured to flow within a vessel at a flow rate that exceeds a physical deformation rate of acoustically deforming the portion of the sample in the direction of flow of the sample.

24. The apparatus of claim 23, further comprising a plurality of non-toxic acoustic scattering elements included within the sample.

25. An apparatus for characterizing a physical property of a sample, the apparatus comprising:
   means for insonifying a portion of the sample in a first direction;
   means for insonifying the portion of the sample in a second direction;
   means for controlling the insonifying to be capable of acoustically bidirectionally deforming the portion of the sample over a deformation range about a neutral-deformation locus within the deformation range;

means for measuring a deformation response of at least a portion of the sample to the insonification; and means for providing an indication characterizing the physical property of the sample using the measured response of at least a portion of the sample to the insonification.

* * * * *